(12) United States Patent
Correale et al.

(10) Patent No.: US 8,344,100 B2
(45) Date of Patent: Jan. 1, 2013

(54) POLY-EPITOPE PEPTIDE DERIVED FROM THYMIDYLATE SYNTHASE HAVING IMMUNOLOGICAL AND ANTI-TUMOUR ACTIVITY

(75) Inventors: Pierpaolo Correale, Siena (IT); Maria Grazia Cusi, Siena (IT); Guido Francini, Siena (IT); Giorgio Giorgi, Siena (IT)

(73) Assignee: Universitá degli Studi di Siena, Siena (IT)

( * ) Notice: Subject to any disclaimer, the term of this patent is extended or adjusted under 35 U.S.C. 154(b) by 931 days.

(21) Appl. No.: 11/814,919

(22) PCT Filed: Feb. 15, 2006

(86) PCT No.: PCT/IT2006/000078
§ 371 (c)(1),
(2), (4) Date: Aug. 25, 2008

(87) PCT Pub. No.: WO2006/087756
PCT Pub. Date: Aug. 24, 2006

(65) Prior Publication Data
US 2008/0305091 A1    Dec. 11, 2008

(30) Foreign Application Priority Data
Feb. 16, 2005   (IT) .............................. RM2005A0064

(51) Int. Cl.
| | |
|---|---|
| *A61K 38/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *A61P 35/00* | (2006.01) |

(52) U.S. Cl. ...................... 530/300; 514/19.3
(58) Field of Classification Search ........................ None
See application file for complete search history.

(56) References Cited

U.S. PATENT DOCUMENTS
8,101,174 B2 * 1/2012 Gatanaga et al. ............ 424/94.1
2005/0033023 A1   2/2005 Correale et al.

FOREIGN PATENT DOCUMENTS
WO      WO02083714       10/2002
WO   PCT/IT2006/000078    8/2006

OTHER PUBLICATIONS

Melief et al., 2008, Nat. Rev. vol. 8: 351-360.*
Johnston et al., 1991, Cancer Res. vol. 51: 6668-6676.*
NCBI ref. seq NP_oo1062.1, 2012, pp. 1-3.*
Bei et al., 2010, J. Biomed. Biotech. vol. 2010, pp. 1-12.*
Le et al., 2001, Vaccine. vol. 19: 4669-4675.*
Correale, In Vitro Generation of Cytotoxic T Lymphocytes Against HLA-A2.1-Restricted Peptides . . . , Journal of Chemotherapy vol. 13 n.5, Italy, 2001.
Ichikawa, Thymidylate Synthase and Dihydropyrimidine Dehydrogenase Gene Expression . . . , Int. J. Cancer, 112, 967-973 (Wiley-Liss 2004).
Correale, 5-Fluorouracil-Based Chemotherapy Enhances the Antitumor Activity . . . , J. Nat'l Cancer Institute, vol. 97, N.19 (Oxford Univ Press 2005).

* cited by examiner

*Primary Examiner* — Amy Juedes
(74) *Attorney, Agent, or Firm* — Lucas & Mercanti, LLP

(57) ABSTRACT

The present invention concerns a peptide having anti-tumour activity and its related pharmaceutical compositions. In particular, the invention concerns a peptide with anti-tumour preventive and therapeutic activity, also in combination with other known anti-tumour compounds such as, for example, 5-fluorouracil.

4 Claims, 7 Drawing Sheets

POLY-EPITOPE PEPTIDE DERIVED FROM THYMIDYLATE SYNTHASE HAVING IMMUNOLOGICAL AND ANTI-TUMOUR ACTIVITY

CROSS-REFERENCE TO RELATED APPLICATIONS

This application is a 371 of PCT IT2006/000078, filed Feb. 15, 2006, which claims the benefit of Italian Patent Appl. No. RM2005A000064, filed Feb. 16, 2005, the contents of each of which are incorporated herein by reference.

TECHNICAL FIELD OF THE INVENTION

The present invention concerns a peptide having anti-tumour activity and its related pharmaceutical compositions. In particular, the invention concerns a peptide with anti-tumour preventive and therapeutic activity, also in combination with other known anti-tumour compounds such as, for example, 5-fluorouracil.

PRIOR ART

Thymidylate synthase (TS) is an intracellular protein capable of regulating itself in response to the expression levels of its co-factors and its substrates. TS is the principal source of thymidine in eukaryotic cells, and necessary for DNA synthesis and duplication. It synthesises thymidine by adding a unit of monocarbonate to deoxyuracil in the presence of reduced folates [1,2].

TS is therefore strictly involved in DNA duplication and in cell proliferation and therefore, in normal cells, its expression is rigorously controlled by genes involved in the cell cycle, and is temporally expressed only during the S phase [3,4].

By contrast, in tumour cells, TS is expressed constitutively and its intensity of expression is an index of proliferation. On the basis of these considerations, some of the most active anti-tumour drugs, including the anti-metabolites, act directly and/or indirectly by inhibiting this enzyme [5].

Furthermore, TS is the critical enzymatic target inhibited by 5-fluorodeoxyuradine monophosphate (5-FdUMP), a metabolite of 5-fluorouracil (5-FU), which is one of the most active cytotoxic drugs and included in almost all of the poly-chemotherapy treatment regimens used to treat malignant neoplasms of the gastroenteric apparatus, breast carcinomas, and malignant neoplasms of the head and neck [6].

5-FU is a fluoropyrimidine pro-drug that has to be activated in the cytoplasm of neoplastic cells into the two cytotoxic metabolites: 5-fluoro-uridine triphosphate (5-FUTP) and 5-FdUMP. The latter is in particular responsible for the permanent inhibition of TS with which, also in association with reduced folate, it forms a stable tertiary complex that is rapidly degraded in the cell cytoplasm by the system of proteasomes responsible for the formation of peptide epitopes derived from tumour antigens.

Many studies have by now demonstrated that the constitutive or acquired over-expression of TS, as well as its mutations, are valid escape mechanisms for tumour cells because they confer resistance to 5-FU [7].

In this regard, numerous studies have already shown that the detection of high levels of TS or of its mutations in patients with gastric or colon carcinomas are predictive of drug resistance and considered negative prognostic factors [8,9].

Even in the tumour cells that constitutively express low or intermediate levels of TS, the enzyme is, in any case, subject to potent self-regulatory activity because, after only five hours' exposure to 5-FU, these cells also show an adaptive response, with a clear and immediate over-expression of the enzyme [10].

It is therefore plain that there is a need to develop a therapeutic tool that can overcome the incapacity of 5-FU, alone or in combination with other chemotherapeutic agents, to eradicate completely the neoplastic disease and thus cure patients with malignant neoplasms, particularly of the breast and gastroenteric apparatus.

SUMMARY OF THE INVENTION

The authors of the present invention have developed an anti-tumour peptide agent with immunotherapeutic activity, designated TS/PP, that can also be combined with conventional fluoropyrimidine-based chemotherapy and is capable of obtaining, in vivo and in vitro, a polyepitope, cytotoxic T-lymphocyte response capable of destroying the tumour cells that over-express the TS enzyme. As the expression of the TS protein is one of the first alterations occurring in all human tumours during carcinogenesis, the peptide of the invention has also a preventive immunoprotective action in addition to its therapeutic activity.

TS/PP is a synthetic peptide 28amer characterised by the fact that it contains various amino acid sequences of an epitope nature, some of which are potentially capable of binding different haplotypes of class I HLA molecules (including the three known epitopes specific for HLA-A(*)02.01 molecules: TS-1, TS-2 and TS-3) [11], and class II HLA molecules. The immunological and anti-tumour activity of TS/PP has been demonstrated in human in vitro models and in mice (transgenic-HHD mice) genetically engineered with human class I molecules of the major histocompatibility system (haplotype HLA-A(*)02.01) that express a TS which is very similar to the human TS (90-95% amino acid similarity).

In the human model, TS/PP has been used to generate cytotoxic T-lymphocyte (CTL) lines in vitro by cyclically stimulating human peripheral blood mononuclear cells (PBMCs) (derived from both normal donors and donors with malignant neoplasms) with low doses of interleukin 2, and in co-cultures with autologous dendritic cells previously exposed to TS/PP. These lymphocytic lines manifest significant cytotoxic activity against breast and colon carcinoma (HLA-A(*)02.01+) tumour cells. This cytotoxic activity dramatically increases if the tumour cells are pre-exposed to sub-lethal doses of 5-FU capable of increasing the endogenous expression of TS.

In the animal model, TS/PP administered to HHD mice inoculated with autologous (EL-4 HHD) leukemic cells expressing TS has potent (preventive and therapeutic) anti-tumour activity that is increased by combined treatment with 5-FU. The immunogenic and anti-tumour activity of TS/PP is not associated with the onset of any adverse event or autoimmunity but, in both the murine and human models, is much greater than that exercised by the known epitope peptides of TS (TS-1, TS-2 and TS-3) used individually or in combination.

The present invention also regards a method for generating in vitro TS-specific (and multi-epitope) CTL lines with anti-tumour activity to be used for the immunotherapy of neoplastic patients. The lymphocytic lines to be reinfused in the neoplastic patients are in fact generated by means of ex vivo cyclic stimulation of the patients' peripheral blood mononuclear cells (PBMCs).

(HLA-(*)02.01+, harvested by means of leukopheresis) with low does of IL-2 and autologous dendritic cells exposed to the TS/PP peptide.

The present invention also regards the capacity of the TS/PP peptide to prevent the onset of tumours in transgenic mice positive for HLA-(*)02.01 (HHD) and inoculated with autologous (EL-4/HHD) tumour cells.

The present invention also regards the capacity of the TS/PP peptide to induce an immune response with anti-tumour activity in transgenic mice positive for HLA-(*)02.01 (HHD) and inoculated with autologous (EL-4/HHD) tumour cells in the absence of an auto-immune and/or toxic response.

Furthermore, the present invention regards the combined TS/PP and 5-FU anti-tumour therapy as a chemo-immunotherapeutic treatment for fluoropyrimidine-sensitive carcinomas (gastroenteric, breast, and head and neck carcinomas).

The object of the present invention is therefore a peptide included in the sequence YMIAHITGLFLDSLGFSTTLGDAHIYL (Seq. Id. No. 2) for medical use. Preferably the peptide has the sequence from amino acid 19 to amino acid 27 of Seq. Id. No. 2, TLGDAHIYL. Alternatively, it has the sequence from amino acid 1 to amino acid 9 of Seq. Id. No. 2, YMIAHITGL. Alternatively, the peptide has the sequence from amino acid 10 to amino acid 18 of Seq. Id. No. 2, FLDSLGFST.

In an alternative preferred form, the peptide has the sequence YMIAHITGLFLDSLGFSTTLGDAHIYL (Seq. Id. No. 2).

A further object of the invention is a vector that includes, and is capable of effectively expressing in an eukaryote cell, a nucleotide sequence coding for the peptide of the invention, in which the nucleotide sequence is preferably TACATGATTGCGCACATCACGGGCCTGTTTTTGGACAGCCTGGGATTCTCCACC ACTTTGGGAGATGCACATATTTACCTG (Seq. Id. No. 1).

A further object of the invention is a pharmaceutical composition with preventive anti-tumour activity that includes a pharmaceutically effective amount of the peptide according to the invention and appropriate excipients and/or diluents and/or solubilising agents.

A further object of the invention is a pharmaceutical composition with chemotherapeutic activity that includes a pharmaceutically effective amount of the peptide according to the invention and appropriated excipients and/or diluents and/or solubilising agents.

Preferably the pharmaceutical composition includes a further anti-tumour active ingredient and, more preferably, the further anti-tumour active ingredient is 5-fluorouracil.

A further object of the invention is a method for obtaining in vitro cytotoxic T-lymphocytes (CTLs) activated for TS, including the following steps:
a) take PBMCs from a subject and culture them in vitro;
b) stimulate the said PBMCs in vitro by exposing them to irradiated autologous dendritic cells, previously exposed for opportune times to efficacious concentrations of the peptide according to the invention itself.

Another object of the invention are cytotoxic T-lymphocytes activated for TS obtainable by means of the described method, preferably for immunotherapy.

The present invention will now be described in its non-limitative examples, with particular reference to the following figures:

Figure 2:
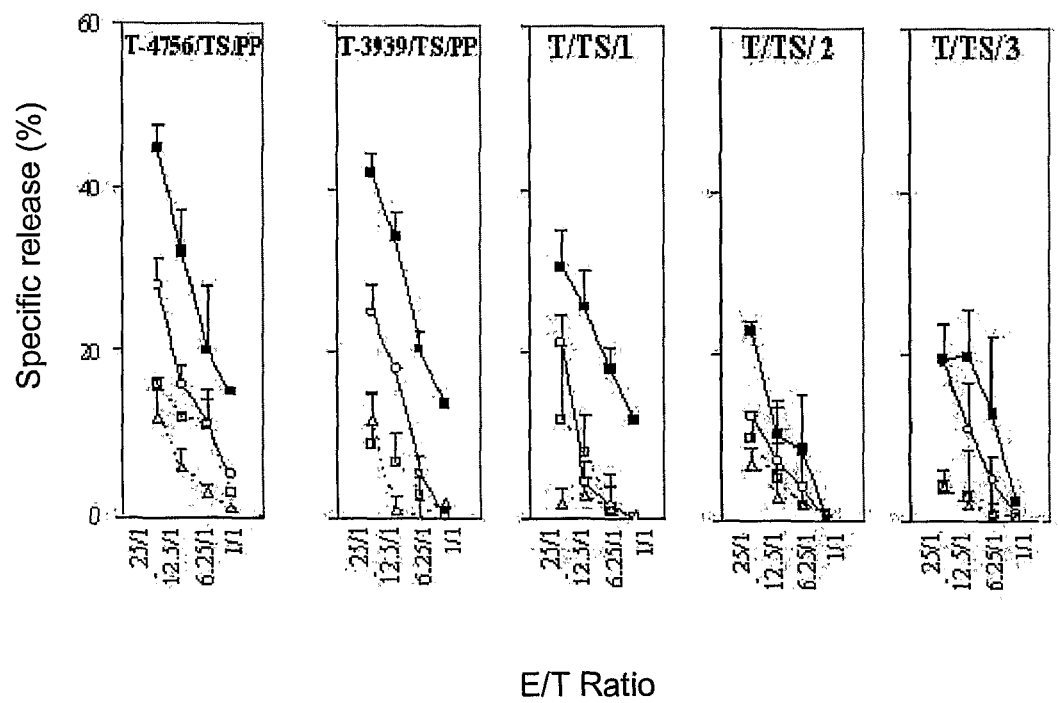

The symbols represent: CIR-A2 target cells not exposed to any reagent [·· ° ··]; CIR-A2 cells transfected with pcTS [———]; CIR-A2 cells exposed to the TS/PP peptide [———]; CIR-A2 cells pulsed with TS-1 [·· ° ··]; CIR-A2 cells pulsed with TS-2 [———]; CIR-A2 cells pulsed with TS-3 [———]; CIR-A2 cells pulsed with PTR-4 [···▫···]. CIR-A2 cells pulsed with the IFN peptide [———];

FIG. 2—The lytic activity of cytotoxic T-lymphocyte lines generated using the TS/PP peptide against breast carcinoma cells is increased by 5-FU pre-treatment of target cells.

Examined in cytotoxicity tests in vitro, the CTL lines generated using TS/PP were capable of killing target cells derived from HLA-A(*)02.01+ breast carcinoma (the MDA-MB-231 cell line). The lytic activity of the effector lymphocytes was significantly greater than that induced by lymphocyte lines generated in vitro using each of the three aforesaid peptide epitopes of TS, and was significantly increased if the target cells had been subjected to sub-lethal 5-FU doses capable of increasing the endogenous expression of TS.

The lytic activity of the specific TS/PP lymphocytes was restricted to class I HLA molecules because it was eliminated if the cytotoxicity experiment was performed in the presence of anti-HLA-(*)02.01 antibodies (A2.69 and W6.32) (data not shown). The lysis was instead not changed by UPC-10 antibody used as a negative control not reacting with the target cells (data not shown in the figure).

The results are expressed as the percentage of specific lysis at different effector/target (E/T) ratios.

The symbols represent: MDA-MB-231 target cells [·· ○ ··]; MDA-MB-231 cells exposed to A2, 69 mAb [—▲—]; MDA-MB-231 cells pretreated with 5-FU [—■—]; MDA-MB-231 cells pretreated with 5-FU and exposed to A2.69 mAb [···■···].

Figure 3:
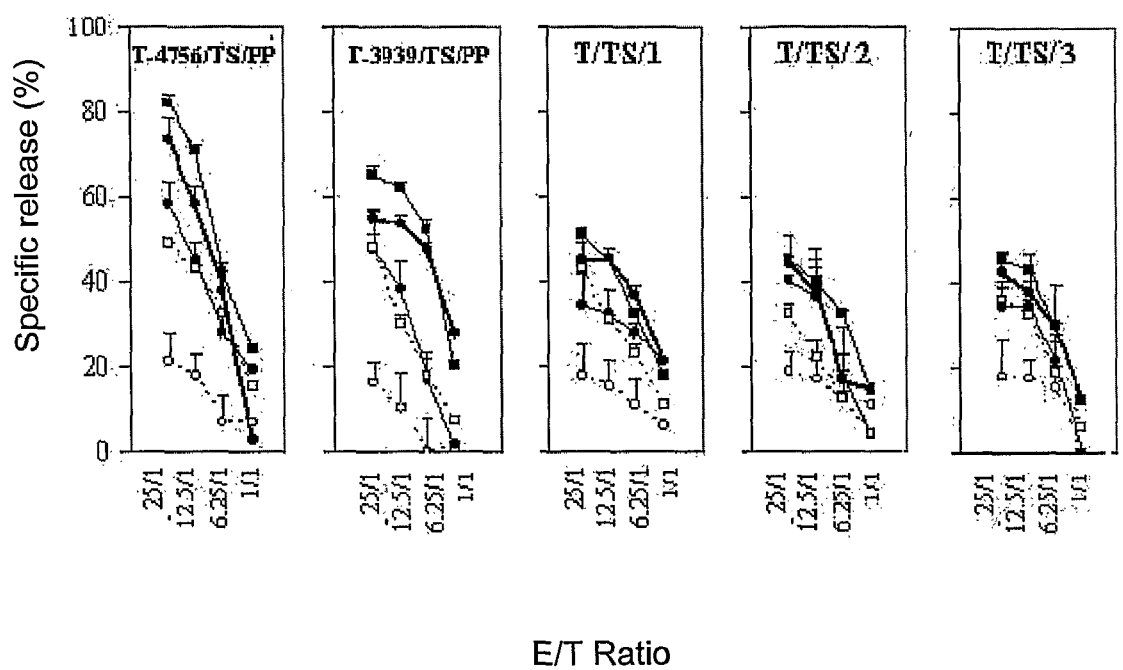

FIG. 3—The lytic activity against colon carcinoma cells of cytotoxic T-lymphocyte lines generated using the TS/PP peptide is increased by 5-FU pre-treatment of the target cells.

The lymphocyte lines generated in vitro using TS/PP were capable of destroying the target cells derived from colon carcinoma (the HT-29 and SW-1463 cell lines). The HT-29 cell line is a colon carcinoma cell line that does not express HLA-A(*)02.01 and can therefore be used as target cells of our CTLs, were induced to express HLA-A(*)02.01 molecules by means of transfection (pc-HLA-A(*)02.01 gene). The lysis induced by the lymphocyte lines generated using the TS/PP peptide was greater than that induced by the other lymphocyte lines generated using each of the three individual epitopes, and was significantly increased when the target cells were subjected to sub-lethal 5-FU doses capable of increasing their endogenous production of TS.

The lysis was restricted to class I HLA molecules because it was eliminated by the use of the A2.69 and W6.32 antibodies in the cytotoxicity tests (data not shown in the figure), and also because these CTLs were incapable of killing the HT-29 cells not transfected with the HLA-(*)02.01 gene, or transfected with plasmid backbone (data not shown in the figure). The results are expressed as the percentage of specific lysis at different effector/target (E/T) ratios.

Figure 4:
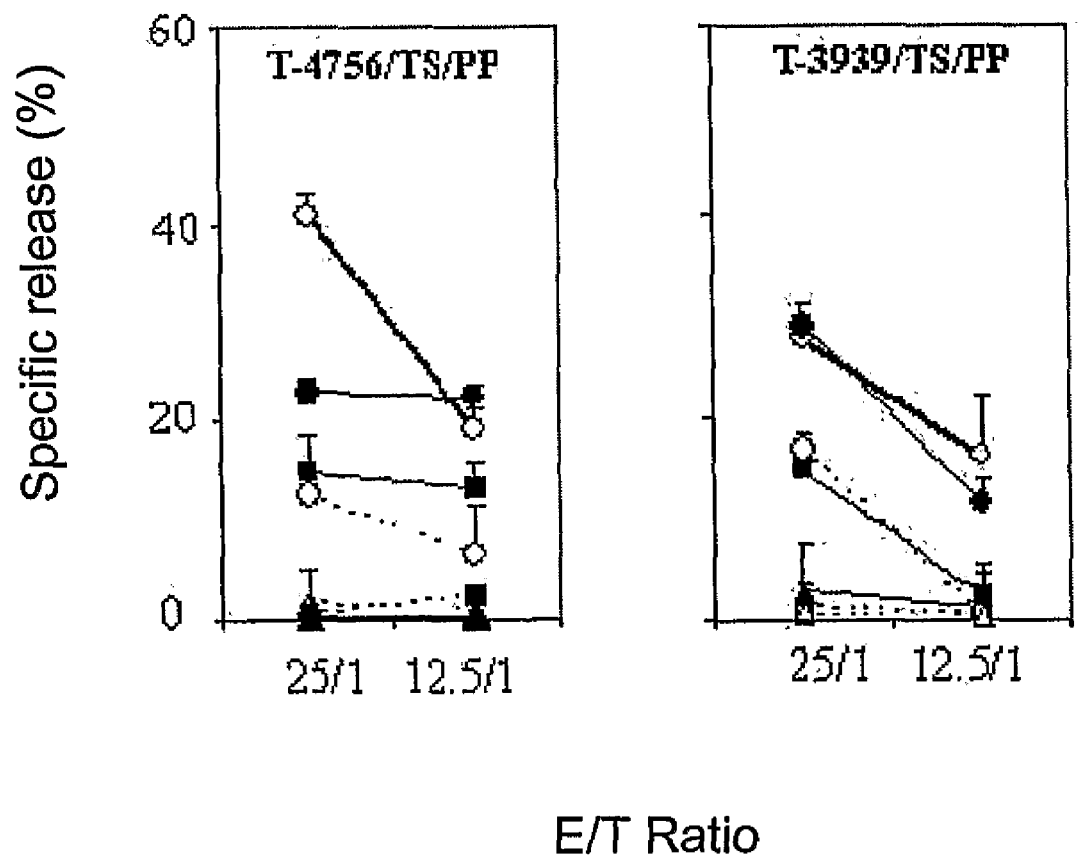

The symbols represent: HT-29 target cells [···■···]. HT-29 cells transfected with the HLA-(*)02.01 gene [—◆—]; HT-29 cells pretreated with 5-FU transfected with the HLA-A(*)02.01 gene HLA-A(*)02.01 [—◆—]; SW-1463 target cells [···■···]. SW-1463 cells pretreated with 5-FU [—■—];

FIG. 4—Peptide specificity of the lymphocyte lines assessed by means of a CTL cold competition assay.

The figure shows the peptide specificity of the two lymphocyte lines generated using the TS/PP peptide examined by means of a cold competition assay by measuring effector/target ratios of 25/1 and 12.5/1, and using CIR-A2 cells pulsed with TS/PP as the target cells of the CTLs (loaded with $^{51}$Cr) and HT-29 cells [transfected with the HLA-A(*)02.01 gene or pretreated with 5-FU and then transfected with the HLA-A(*)02.01 gene] as cold competitors used at scalar labelled-target/cold competitor (L/C) ratios.

The figure shows that the cytotoxic activity of the CTLs against the CIR-A2 cells loaded with 25 □g/ml of TS/PP was reduced by the cold competitors and completely eliminated at lower L/C ratios [1/5] [P<0.05]. The figure also shows that the HT-29 cells pretreated with 5-FU and then transfected with the HLA-A(*)02.01 gene were much more efficient as they eliminated the lysis of the target cells at a five-fold higher L/C ratio [1/1] [P<0.05]. This suggests that the immunosensitising effect of 5-FU is indeed related to the increased amount of TS epitopes in the target cells.

Figure 5:
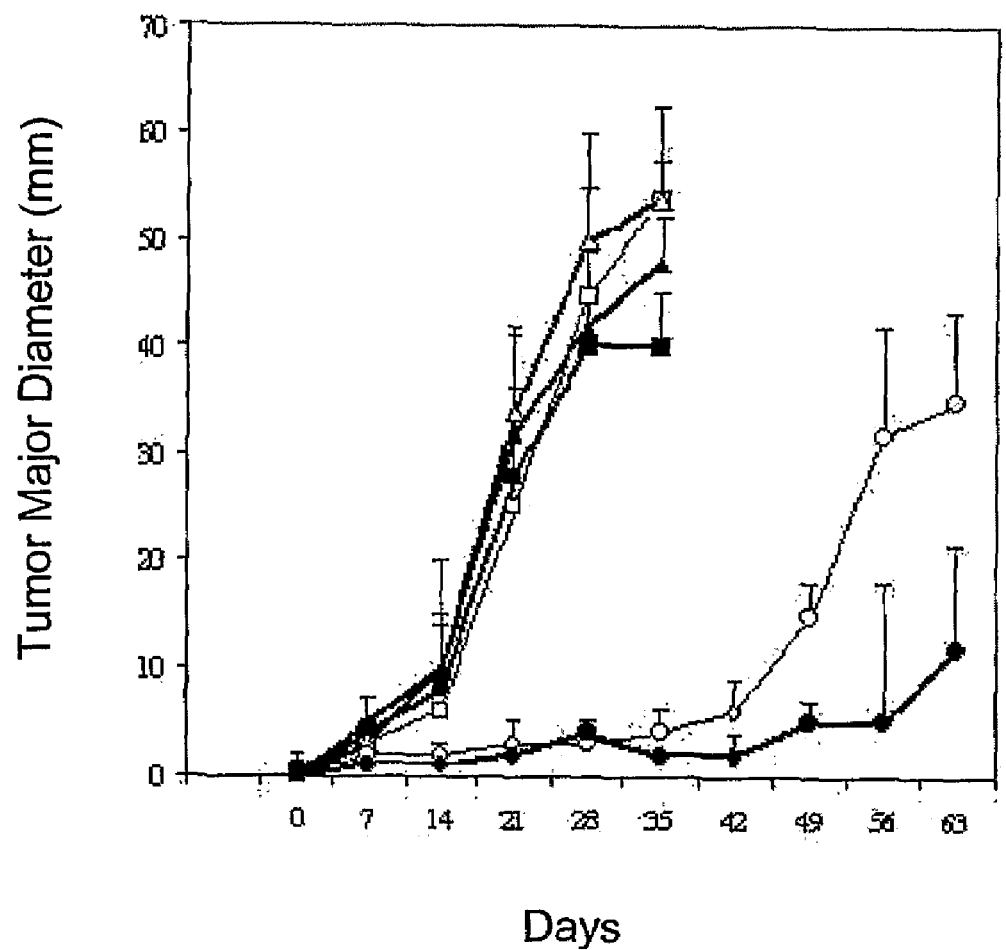

The symbols represent the CIR-A2 target cells loaded with TS/PP in the presence of: no competitor [·· ○ ··]; HT-29 cells transfected with the HLA-A(*)02.01 gene and used as cold competitors at L/C ratios of 1/1 [—◆—], 1/2 [—■—]; and 1/5 [—▲—]; HT-29 cells pretreated with 5-FU and then transfected with the HLA-A(*)02.01 gene and used as cold competitors at L/C ratios of 1/1 [·· ○ ··]; 1/2 [—■—]; and 1/5 [—▲—];

FIG. 5—Tumour growth in HHD mice inoculated with autologous leukemic cells is significantly slowed or totally abrogated by combined treatment with TS/PP and 5-FU.

Tumour growth was monitored weekly by measuring its maximum diameter. The results are given as the mean value ±SD of the maximum diameter. The mice vaccinated with TS/PP showed a significant delay in tumour growth, which became even more evident in the mice receiving TS/PP together with chemotherapeutic treatment with 5-FU.

In these experiments, the chemotherapeutic treatment alone, vaccination with the control peptide (derived from the mumps virus), and vaccination with a combination of the three TS peptide epitopes (+/−5-FU) were all incapable of preventing neoplastic growth.

Figure 6:
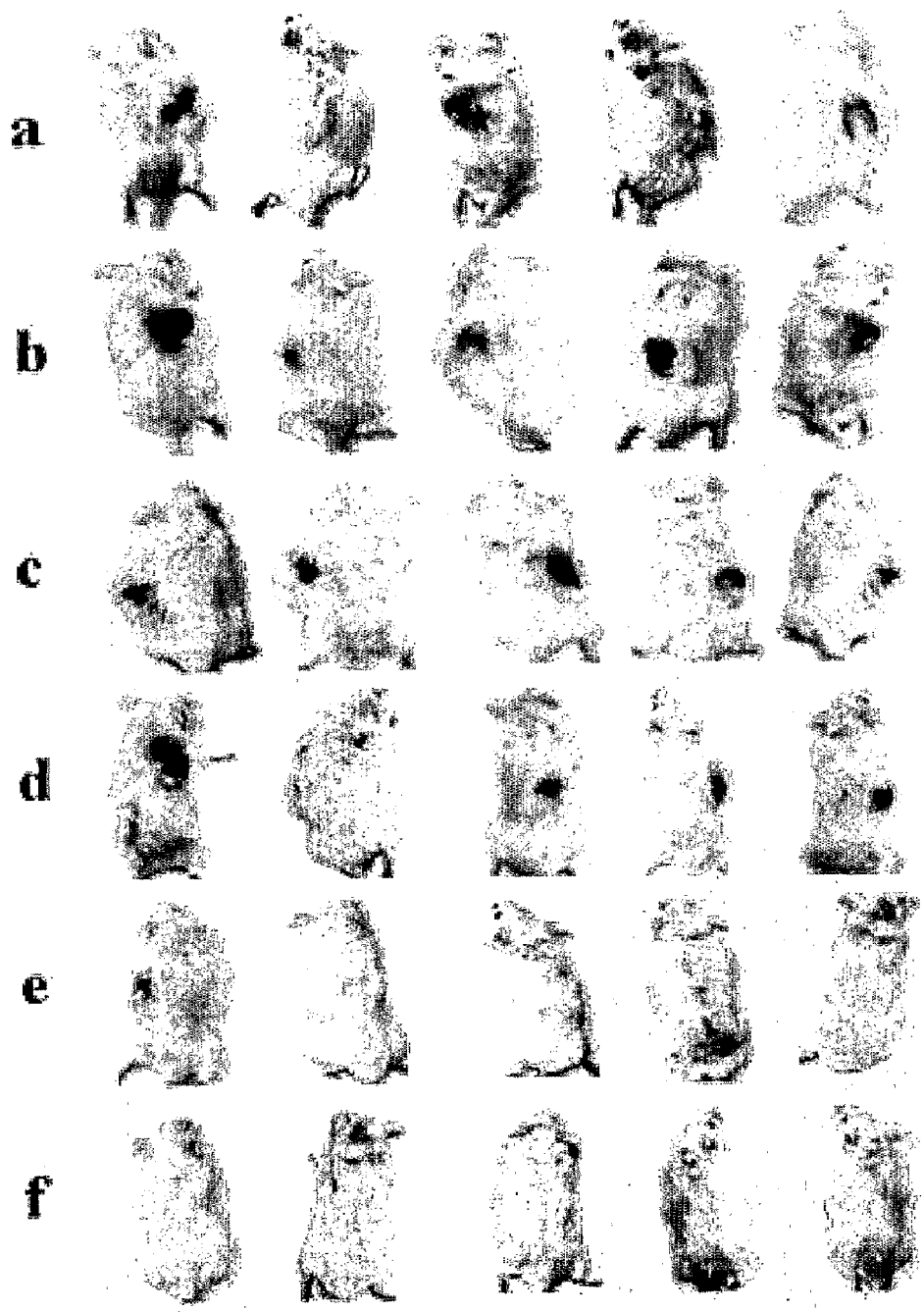

The symbols represent a group of mice treated with: the control peptide [···■···]. a cocktail of TS peptide epitopes [—▲—]; the TS/PP peptide [·· ○ ··]; the control peptide and 5-FU chemotherapy [—■—]; the cocktail of TS peptide epitopes and 5-FU chemotherapy [—▲—]; the TS/PP peptide and 5-FU chemotherapy [—◆—];

FIG. 6—The figure shows the appearance of the tumour in each mouse belonging to the different groups 30 days after subcutaneous inoculation with 2×10$^6$ autologous leukemic cells (EL4/HHD). This experiment shows that combined treatment with TS/PP and 5-FU has the greatest anti-tumour and protective activity. The photograph shows anesthetised mice. The experiment was repeated twice with the same results.

A: Mice vaccinated with the control peptide (mumps).
B: Mice vaccinated with the control peptide and treated with 5-FU.
C: Mice vaccinated with the cocktail of TS peptide epitopes.
D: Mice vaccinated with the cocktail of TS peptide epitopes and treated with 5-FU.
E: Mice vaccinated with the TS/PP peptide.
F: Mice vaccinated with the TS/PP peptide and treated with 5-FU.

Figure 7:
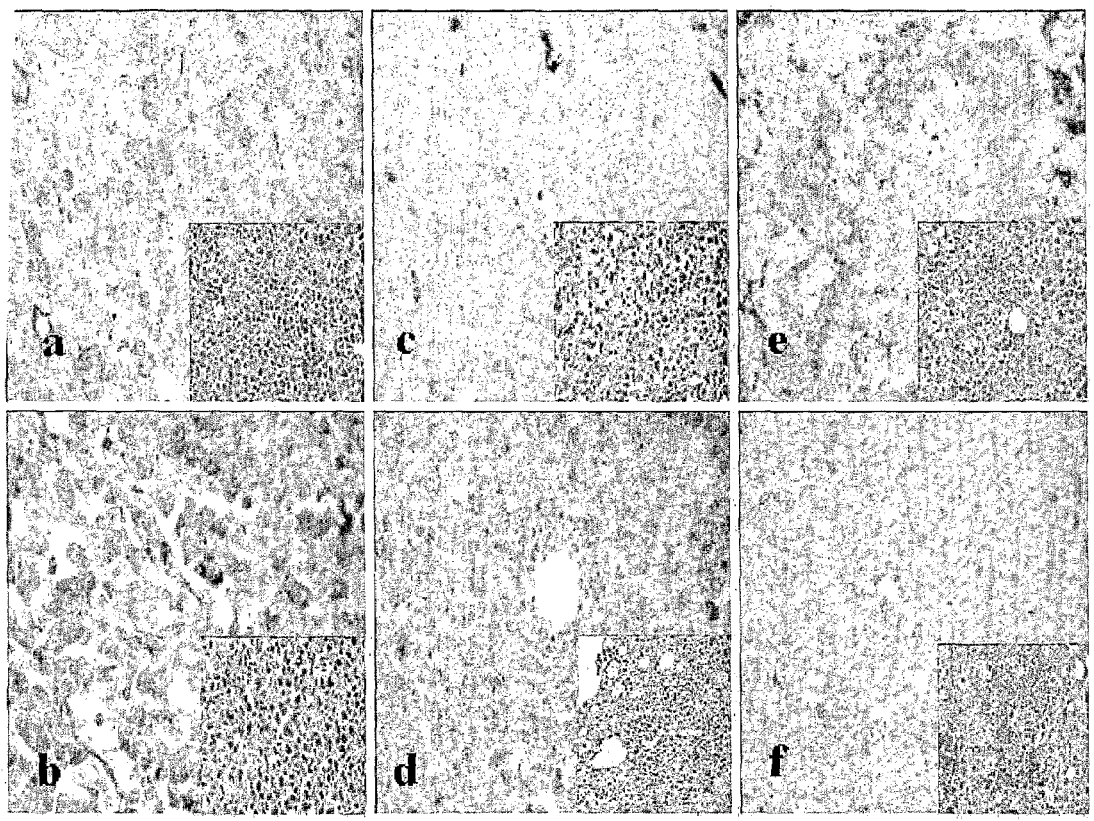

FIG. 7—The figure shows the results of an anatomo-pathological study of tumour tissue taken from sacrificed animals. The larger photograph shows immunostaining for TS (IS), whereas the smaller inset photograph shows hematoxylin and eosin staining (HES) on the same sample. Each picture comes from a single animal and is representative of the anatomo-pathological condition encountered in the group of animals receiving the same treatment.

A: Mice vaccinated with the control peptide (mumps). IS: Presence of tumour cells highly positive for TS expression; HES: Layer of tumour cells with a few apoptotic bodies.
B: Mice vaccinated with the control peptide and treated with 5-FU. IS: Increased number of tumour cells positive for TS expression; HES: Degenerative alterations in tumour cells and presence of intercellular spaces.

C: Mice vaccinated with the cocktail of TS peptide epitopes. IS: Rare tumour cells positive for TS expression and groups of small lymphocytes surrounding the TS-negative areas; HES: Many apoptotic bodies, intercellular spaces and presence of a desmoplastic reaction.

D: Mice vaccinated with the cocktail of TS peptide epitopes and treated with 5-FU. IS: Rare TS-positive tumour cells and agglomerates of small lymphocytes in the TS-negative areas; HES: pseudocystic spaces in areas with conspicuous degenerative changes.

E: Mice vaccinated with the TS/PP peptide. Rare TS-positive cells and agglomerates of small lymphocytes surrounding the TS-negative areas and infiltrating the spaces between the remaining tumour cells; HES: diffuse pseudocystic areas throughout the neoplastic tissue.

F: Mice vaccinated with the TS/PP peptide and treated with 5-FU. Almost no TS-positive cells and many agglomerates of small lymphocytes surrounding the TS-negative areas; HES: agglomerates of small lymphocytes between the cells; large and diffuse pseudocystic areas throughout the neoplastic tissue.

MATERIALS AND METHODS

Cell cultures. The MDA-MB-231 breast carcinoma cell line, and the HT29 and SW-1463 colon carcinoma cell lines were purchased from the ATCC. The C1R-A2 lymphoblastoid cell line [12] was donated by Dr. Jeffrey Schlom (EOS, LTIB, NCI, NIH, Bethesda, Md., USA). All of the tumour cell lines were maintained in culture as previously described [12]
*Peptide synthesis*. The TS-derived peptides, TS-1 (TLGDAHIYL) (aa. 19-27 of Seq. Id. No. 2, corresponding to aa. 245-253 of TS), TS-2 (YMIAHITGL) (aa. 1-9 of Seq. Id. No. 2, corresponding to aa. 229-237 of TS), and TS-3 (FLDSLGFST) (aa. 10-18 of Seq. Id. No. 2, corresponding to aa. 111-119 of TS), and TS/PP (YMIAHITGLFLDSLGFSTTLGDAHIYL) (Seq. Id. No. 2) were synthesised chemically and characterised as previously described [14].

The TS-1, TS-2 and TS-3 peptides were selected on the basis of their close binding with HLA-A(*)02.01, as calculated using the algorithm suggested by Parker et al. [15].

Dendritic cell generation and CTL cultures. The l PBMCs were obtained by means of separating buffy coat Ficoll-Hypaque gradients, or from blood samples collected from healthy donors with the HLA-A(*)02.01 haplotype and patients with colon cancer. The dendritic cells used to stimulate the T lymphocytes in vitro were generated from autologous PBMCs grown in the presence of GM-CSF and interleukin 4 as previously described [16].

The PBMCs used to generate the CTL line were cultured as described in previous studies [17] except for the fact that the dendritic cells used to stimulate the CTLs were exposed to TS/PP for four hours before being used for the stimulation (PBMC/CTL co-culture). The irradiated autologous dendritic cells were loaded with the peptides and added to the lymphocyte culture to obtain a final concentration of 1:5 dendritic cells per CTL.

Cytotoxic assays. The release of radioactive chrome ($^{51}$Cr) was assayed as described in previous studies [18].

HLA-A (*)02.01 expression was induced by gene transfection on the membrane of HT29 target cells before every experiment. Specific lysis was calculated as follows:

$$\% \text{ specific lysis} = \frac{\text{observed release} - \text{spontaneous release}}{\text{total release} - \text{spontaneous release}} \times 100$$

Spontaneous release was determined in the plates to which 100 µl of medium was added without effector cells. The total radioactivity released was determined after treating the target with Triton x-100. HLA was blocked by using an anti-HLA-A2 antibody (A2.69, One Lambda, Inc., Chanoga Park, Calif., USA) or the anti-class I (pan A,B,C)-HLA antibody W6.32, which were incubated with the target cells for one hour before the cytotoxicity assay. The negative control was the UPC-10 monoclonal antibody.

Flow cytofluorimetry. The procedure for the cytofluorimetric analysis of each staining has been previously described [19].

The conjugated antibodies were supplied by Becton Dickinson (San Jose, Calif., USA), whereas the W6/32 (anti-class I HLA), A9 (anti-HLA-A2.1), COL-1 (anti-CEA) and MOPC-21 antibodies were respectively supplied by Scra (Sussex, England), One Lambda, and Cappel/Organon Tecknica Corporation, West Chester, Pa., USA). The samples were analysed using a Becton Dickinson FACScan equipped with a blue laser with an excitation level of 15 nW at 488 mm.

Determination of precursor frequency. The dimer cytofluorimetry assay kit and related reagents were supplied by Pharmigen BD, and the tests were carried out as described by the producer [20]).

Statistical calculations. The differences were statistically analysed Stat View statistical software (Abacus Concepts, Berkeley, Calif., USA). The results were expressed as the mean values ±SD of four determinations made in three different experiments, and the differences analysed by means of a two-tailed Student t test or paired samples. A P value of less than 0.05 was considered statistically significant.

Results
Immunological Characterisation of the Poly-Epitope Peptide

The authors characterised the immunological activity of a new poly-epitope peptide construct (TS/PP) containing in succession the amino acid sequences of three peptide epitopes of TS, know as TS-1, TS-2 and TS-3 [21], with a specific binding motif for the HLA-A(*)02.01 molecule. In previous studies, the authors demonstrated that these peptides can bind the HLA-A(*) 02.01 molecule using the T2 test, a cytofluorimetric technique that is capable of indirectly evaluating peptide binding to the HLA molecules on T2 cells, which manifests itself as an increase in the cell membrane expression of these molecules. Each of the three peptide epitopes (TS-1, TS-2 and TS-3) could therefore be used to generate in vitro TS-specific CTL lines with moderate antitumour activity against breast and colon carcinoma cells.

The new-generation TS/PP peptide was developed by uniting the amino acid sequences of the three previously described TS epitopes in a non-progressive succession, thus giving rise to a peptide with an unknown sequence. In its native form, the 28-amino acid TS/PP peptide is incapable of binding the HLA-A 02.01 molecule in the T2 test, and requires processing by professional antigen presenting cells (e.g. B lymphocytes or dendritic cells) in order to give rise to a specific TS multi-epitopec lymphocyte response.

Further analysis of the 28-amer peptide (TS/PP) using the algorithm of Ken Parker revealed that it also contained amino acid sequences belonging to other potential epitopes with specific binding motifs for other common haplotypes of class I and class II HLA (Table 1).

TABLE 1

| Name of peptide | Amino acid Sequence | Aa. position in relation to the native TS sequence | sHLA-A(*)02.01 binding assay (T2 test) | [a]Predicted epitopes potentially capable of binding class I HLA haplotypes |
|---|---|---|---|---|
| TS-1 | TLGDAHIYL | 245-253 | +++ | A2 |
| TS-2 | YMIAHITGL | 229-237 | +++ | 1, A2; 1, A1 |
| TS-3 | FLDSLGFST | 111-119 | +++ | A2 |
| TS/PP | YMIAHITGLFLDSLGFSTTLGDAH IYL (Seq. Id. No. 2) | | – | 5, A2; 1, A3, 1, A1; 5, A24, 1, B44, (and 8, [b]HLAa-Dr) |
| Positive control (CEA) peptide CAP-1 | YLSGANLNL (Seq. Id. No.3) | | +++ | A2 |

[a]predicted by the algorithm of Ken Parker;
[b]predicted by the algorithm of H.G. Rammensee (H.G. Rammensee, J. Bachmann, and S. Stevanovic, in the book "MHC Ligands and Peptide Motifs").

Generation and Characterisation of TS-Specific, Cytotoxic T Lymphocyte Lines Using TS/PP In order to evaluate the immunological activity of the TS/PP peptide, various CTL lines were generated.

The PBMCs of two different HLA-A (02.01)+ donors were cyclically stimulated with autologous dendritic cells exposed to TS/PP (five days of co-culture) and subsequently grown for ten days in a medium containing low doses of interleukin 2 (IL-2) before being stimulated once again. The five days of co-culture +10 days of proliferative stimulation with IL-2 represent one cycle of in vitro stimulation (IVS).

With the aim of obtaining a comparative control, cytotoxic T lymphocyte lines were generated in vitro using the three peptide epitope TS-1, TS-2 and TS-3, starting from the PBMCs of the same donors and using the same methodology. After 4 IVS cycles (two months of culture), the CTL cell lines were considered sufficiently stable to be characterised immunocytofluorimetrically and functionally (cytotoxic activity).

Antigen Processing and Immunogenicity of the TS/PP Peptide

In previous studies, the authors demonstrated that another trentameric peptide containing multiple epitopes for the prostate-specific antigen (PSA) could be processed on the membranes of dendritic cells and target cells to form the individual epitope peptides. This oligo-peptide of PSA could be used to generate multi-epitope PSA-specific lymphocyte lines showing anti-tumour activity in in vitro human models, and then used to give rise to a PSA-specific lymphocyte response in transgenic mice expressing molecule HLA-A(*)02.01 [22]. However, it was not clear whether these results could be extrapolated to other systems.

Figure 1:
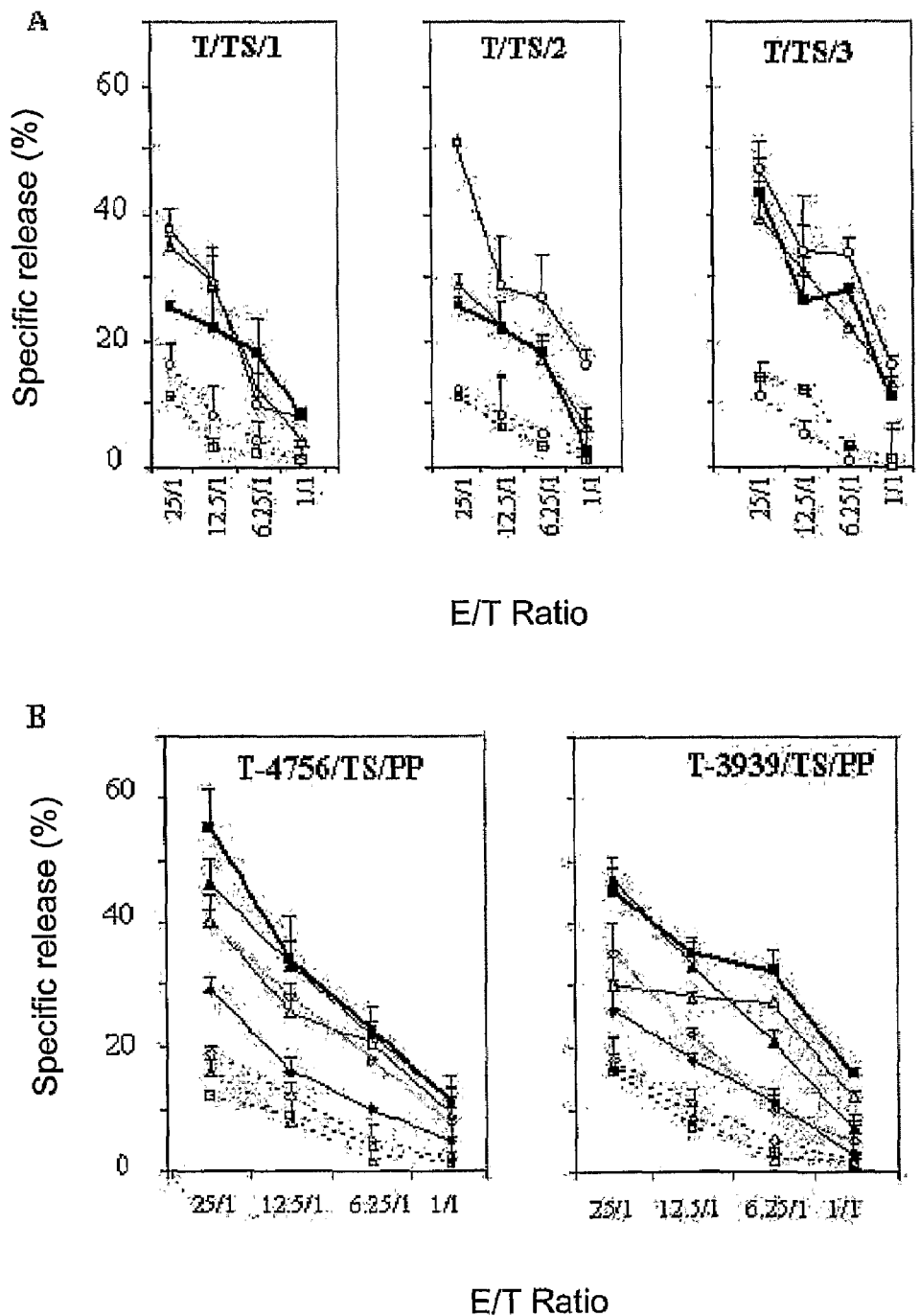
FIG. 1A—The CTL lines generated using each individual epitope peptide of TS (TS-1, TS-2 and TS-3) are capable of lysing CIR-A2 target cells exposed to the TS/PP peptide. These results suggest that TS/PP is processed by the target cells in the form of the individual peptide epitopes. The lytic activity of these CTLs has been examined (by means of the release of $^{51}Cr$) in tests of cytotoxicity against CIR-A2 cells exposed to 25 μg/ml of TS/PP for 4 hours. The positive controls consisted of the same cells, pulsed with 25 μg/ml of each of the individual peptides (TS/1, TS/2, or TS/3) specifically used to generate the lines transfected with a plasmid containing the TS gene (pcTS) that induced overexpression of the enzyme. The negative controls consisted of the same CIR-A2 cells, not exposed to any reagent, transfected with the plasmid backbone (pcDNA3) (data not shown in the figure), or pulsed with a known epitope peptide (PTR-4, parathyroid hormone-related protein) derived from an antigen not expressed in these cells and unrelated to TS. The results are expressed as the percentage of specific lysis at different effector/target (E/T) ratios (mean values and standard deviations of the triplicates of the individual experiments). The symbols represent: untreated target CIR-A2 cells [·· ° ··]; CIR-A2 cells transfected with pcTS [·· ° ··]; CIR-A2 cells pre-exposed to the TS/PP peptide [———]; CIR-A2 cells pulsed with the specific peptide epitopes of TS used to generate the lines [———]; CIR-A2 cells pulsed with the control peptide (PTR-4) [···▫···].
FIG. 1B—Multi-epitope specificity of the CTL lines generated using TS/PP. In cytotoxicity tests, the CTL lines generated using the TS/PP peptide are capable of lysing CIR-A2 target cells pulsed with 25 μg/ml of each of the three peptide epitopes of TS (TS/1, TS/2, or TS/3). CIR-A2 cells exposed to 25 μg/ml of TS/PP for 4 hours, and those transfected with the recombinant plasmid for the TS gene (pcTS), were used as positive controls, whereas the negative controls were the same CIR-A2 cells, not exposed to any reagent or transfected with the plasmid backbone (pcDNA3) (data not shown in the figure), pulsed with PTR-4 or with an epitope peptide derived from the matrix of the influenza virus (IFN). The results are expressed as the percentage of specific lysis at different effector/target (E/T) ratios (mean values and standard deviations of the triplicates of the individual experiments).

The authors have now studied the processing of TS/PP on target cells and evaluated its capacity to give rise to a multi-epitope TS-specific CTL response in vitro. The authors then investigated whether CIR-A2 target cells loaded with the TS/PP peptide were recognized in cytotoxicity tests by the CTL lines generated using each of the three peptide epitopes of TS (TS-1, TS-2, TS-3). The authors observed that each of these lymphocyte lines was capable of killing the target cells exposed to TS/PP. In these experiment, CIR-A2 cells loaded with the same epitope peptide (TS-1, TS-2, TS-3) as that used to generate the examined CTL line, or transfected with a plasmid containing the TS gene (pcTS), were used as positive controls. CIR-A2 cells not exposed to any agent, or exposed to peptides unrelated to TS, or transfected with the plasmid backbone (pcDNA3), were used as negative controls (FIG. 1 and data not shown).

The results of these experiments demonstrated that all three CTL lines (T-TS-1, T-TS-2, T-TS-3) were capable of destroying the target cells exposed to TS/PP and the positive controls (FIG. 1A), but they were not capable of destroying the negative controls. These results suggest that TS/PP is processed by the CIR-A2 target cells, which are then capable of exposing the derived epitopes bound to HLA-A (*) 02.01, thus allowing their recognition by the epitope-specific CTLs.

As previously described, TS/PP was used to generate CTL lines starting from HLA-A02.01+ donors; these CTLs, designated T3939/TS/PP and T4756/TS/PP had the following immunophenotypes: CD3+=90-95%; CD56+=10-22%; CD4+=37-40%; CD8+=40-50%. These lymphocyte lines also had multi-epitope cytolytic activity insofar as they were capable of destroying CIR-A2 target cells individually exposed to each of the three known epitopes of TS, and they were also capable of destroying the target cells loaded with TS/PP or transfected with the aforesaid plasmid containing the TS gene. However, the same CTLs were incapable of killing the target cells used as negative controls (FIG. 1B). These data indicate that the TS/PP peptide can also be processed by dendritic cells and can be used to stimulate in vitro a multi-epitope and TS-specific cytotoxic T lymphocyte response.

Anti-Tumour Activity of the Cytotoxic T Lymphocyte Lines Generated Using TS/PP

The lytic activity of the CTL lines generated using TS/PP was examined against HLA-A(*)02.01+ breast and colon carcinoma cells.

The authors also assayed the lytic activity of the CTL lines generated using TS/PP against the same tumour target cells after treatment with sub-lethal doses of 5-FU.

The authors also compared the cytotoxic activity against the same tumour target cells of the CTL lines generated using TS/PP with that of those generated using the individual peptide epitopes TS-1, TS-2 and TS-3. The cytotoxicity tests carried out using the technique of $^{51}$Cr release were performed using target cells coming from cell lines derived from breast carcinoma (MDA-MB-231) and colon carcinoma (HT-29 and SW-1463), before and after treatment with sub-lethal doses of 5-FU.

HT-29 cells do not constitutively express HLA-A(*) 02.01, and so they were used as targets after being transfected with the HLA-A(*)02.01 gene.

The authors demonstrated that the CTL lines generated using TS/PP were capable of killing the MBA-MB-231 cells (FIG. 2), the HT29 cells transfected with the HLA-A(*)02.01 gene, and the SW-1463 cells (FIG. 3).

The lytic activity of the CTLs was restricted to HLA-A(*) 02.01+ molecules because it was eliminated by blocking antibodies (A2.69 and W6.32), and also because the CTLs were incapable of killing the HT29 target cells not transfected with HLA 02.01, or transfected with the plasmid backbone.

The anti-tumour activity of the CTL lines generated using the TS/PP peptide was significantly greater than that of the three CTL lines generated using the three epitope peptides of TS (FIGS. 2 and 3).

Recent studies have found that the expression of TS is modulated by its co-factors and by substrate levels and so, after inhibition induced by the metabolites of 5-FU in tumour cells, the expression of its gene is significantly increased (data not shown in the figures) [23]. The authors therefore investigated whether treatment with 5-FU may sensitise breast and colon cancer cells to the lytic activity induced by the TS-specific CTLs. Using the same cytotoxicity tests described above, the authors demonstrated that, when exposed to sub-lethal doses of 5-FU for 48 hours, the same breast and colon carcinoma tumour cells were significantly more sensitive to the cytotoxic activity of the CTLs generated using TS/PP and/or the other TS epitopes.

The lytic activity of the CTLs against the target cells treated with 5-FU was always restricted to class I HLA molecules because it was reduced or eliminated by the use of a blocking antibody (A2.69).

Also in this case, the lytic activity of the lymphocyte lines generated using TS/PP was greater than that of the lymphocyte lines generated using the individual peptide epitopes TS-1, TS-2 and TS-3 (FIGS. 2 and 3).

The viability of the target cells exposed to 5-FU was examined by means of a hemocytometric count after staining and was never less than 90%, thus excluding the possibility that the immunosensitisation was due to the large number of dead or already degenerating cells in the cytotoxicity assay.

Cytofluorimetric and immunoblotting analyses of the target cells showed that the treatment with 5-FU did not induce any change in class I HLA expression, but was capable of inducing a significant increase in TS expression in the MDA-MB-231, HT-29 and SW-1463 target cells (data not shown).

The CTL-Mediated Lysis of Breast and Colon Carcinoma Cells is Conditioned by the Presence of Peptide Epitopes of TS In an attempt to demonstrate that the cytolytic activity of the lymphocytes generated using TS/PP against breast and colon carcinoma tumour cells is a specific phenomenon of the interaction between TS and HLA-A(*)02.01 molecules, the authors performed cold antigen competition assays by carrying out cytotoxicity tests in which CIR-A2 cells exposed to TS/PP (labelled with $^{51}$Cr) were used as targets of the CTL effectors and HT29 colon carcinoma cells transfected with HLA-A (*)02.01, or transfected and subsequently exposed to sub-lethal doses of 5-FU, were used as cold (unlabelled) competitors. In cytotoxicity tests, the target cells and the cold competitors were used in different L/C ratios.

These experiments demonstrated that the CTL-mediated lysis of the CIR-A2 cells loaded with TS/PP was reduced by the addition of the cold competitors in cytotoxicity tests, and completely abolished when the L/C ratio reached the value of 1/5. If competitors treated with 5-FU were added to the cytotoxicity test, CTL-mediated lysis of the target cells (CIR-A2 cells loaded with TS/PP) occurred at a five-fold lower L/C ratio (1/1) (FIG. 4). Similar results had been previously obtained using MDA-MB-231 breast carcinoma cells (data not shown).

The results of these experiments suggest that the lymphocyte lines generated using TS/PP recognise (on the membrane of the CIR-A2 cells loaded with TS/PP and on the tumour cells) the same peptide epitopes bound to HLA-A(*) 02.01 molecules as those contained in the TS/PP sequence. These results suggest that the immunosensitisation induced by 5-FU is related to increased TS production, and therefore a greater accessibility of the peptide epitopes to the HLA molecules, as a direct consequence of over-regulation of TS in the cytoplasm of the target cells.

In Vivo Study of Mice Engineered to Express HLA-A(*) 02.01 Molecules

The authors examined the immunological, toxicological and anti-tumour activities of TS/PP in transgenic (HHD) mice genetically engineered to express human HLA-A(*) 02.01 molecules.

The authors also compared the immunological, toxicological and anti-tumour activities of TS/PP with those induced by a combination of the three known peptide epitopes of TS (TS-1, TS-2 and TS-3).

In this study, six groups of five mice received different immunological treatments with or without chemotherapeutic treatment with 5-FU. The mice in groups A and B were administered a control peptide derived from the mumps virus (100 µg per mouse); the mice in groups C and D were administered a cocktail of the TS-1, TS-2 and TS-3 peptides (100 µg per mouse); and the mice in groups E and F were administered the TS/PP peptide (100 µg per mouse).

The mice received the first peptide administration subcutaneously at time 0, with recalls in the third and sixth week. Two weeks after the last administration, all animals were subcutaneously inoculated with $2 \times 10^6$ EL-4/HHD cells.

Before the inoculation of EL-4/HHD cells, autologous lymphoblastic cells for HHD mice expressing the HLA-A(*) 02.01 haplotype were tested for the endogenous expression of TS and HLA by means of cytofluorimetric tests that revealed a low constitutive expression of murine TS (35%). However, this expression could be significantly increased by the treatment with sub-lethal dose of 5-FU (up to 55-70%). In order to evaluate the possible interaction between TS and the 5-FU treatment for vaccination purposes, seven days after the tumour cells inoculation, the mice in groups B, D and F underwent a chemotherapeutic treatment based on weekly intraperitoneal administration of 5-FU (100 □g/ml per mouse). The results of the study demonstrated that TS/PP treatment significantly delayed neoplastic growth, whereas when the TS/PP treatment further include chemotherapeutic treatment the majority of the mice were cured (FIGS. 5 and 6). On the contrary, the chemotherapy alone and the treatment with the combination of TS epitopes, with or without chemotherapy, did not change neoplastic growth in any way.

In fact, 30 days after the inoculation of the tumour cells, the mice in groups A, B, C and D (treated with the control peptide or the combination of peptides +/−chemotherapy) developed a large tumour mass and their clinical condition rapidly declined; for this reason, they were sacrificed.

The most evident anti-tumour effect was observed in the group of mice treated with TS/PP. Some of these mice started to develop a small tumor only 35-40 days after the inoculation, time by which the control mice treated or not with 5-FU had already died of the disease or had been sacrificed. The anti-tumour effect of the TS/PP vaccination was even more efficient in mice that had received 5-FU treatment. Indeed in this group, tumour mass was totally absent in 3 out of 5 mice. In the mice of this group which develop a tumour, the mass did not adhere to the subcutaneous tissue or muscle fascie, and could be radically removed surgically. In this case, the mice could be kept alive and remained in good condition without any further pathological signs for the next 30 days, when they were sacrificed for the immunological and anatomo-pathological studies.

The anti-tumour activity of the splenocytes derived from the mice vaccinated with TS/PP or the combination of peptides, and then sacrificed, was demonstrated in cytotoxicity tests ($^{51}$Cr) against EL-4/HHD (data not shown in the figure).

Dimer cytofluorimetry of the mice vaccinated with TS/PP or the combination of the three peptides demonstrated effective specific immunisation against the three TS epitopes.

TABLE 2

| Peptide-specific CTL precursors | Mouse treatments | | | |
|---|---|---|---|---|
| | Control spleen cells | Control mumps virus peptide | TS/PP peptide | Combination of TS peptides |
| TS/1 | 0.3 (±0.1)/ 3500 | 0.4 (±0.2)/ 4375 | 1.1 (±0.1)/ 9050 | 1.2 (±0.2)/ 9049 |
| TS/2 | 0.2 (±0.1)/ 2700 | 0.4 (±0.1)/ 5414 | 1.5 (±0.3)/ 9050 | 1.3 (±0.1)/ 8105 |
| TS/3 | 0.3 (±0.1)/ 4000 | 0.6 (±0.1)/ 4888 | 1.5 (±0.3)/ 7880 | 0.9 (±0.05)/ 8361 |

The results are expressed as the percentage of CD8$^+$/specific dimeric peptide$^+$ (PE/dimer) in relation to the mean fluorescence per cell. The numbers in brackets correspond to the standard deviations Anatomo-pathological study of the tumour tissue of the animals in the control group revealed moderate TS expression in the neoplastic cells, which was further increased by the chemotherapeutic treatment. However, although capable of increasing necrosis and apoptosis, the latter did not have any significant effect on tumour growth, whereas vaccination with the combination of TS epitopes or TS/PP led to significant lymphocytic infiltration and a reduction in, or the disappearance of tumour cells expressing TS.

Combined treatment with TS/PP and chemotherapy not only led to the disappearance of TS from the neoplastic cells, but also to the clear immunomediated destruction of the tumour tissue, which was rich in degenerative pseudocysts and lymphocytic infiltration (FIG. 7). Anatomo-pathological study of organs such as lung, liver, spleen, kidney and brain, skin and mucosa did not reveal any sign of degeneration or autoimmunity in any of the examined groups.

All of these results suggest that TS/PP is capable of inducing a cell-mediated response with potent anti-tumour activity in vivo that is better than that induced by the combination of TS1, TS2 and TS3. TS/PP works better if administered in concomitance with 5-FU treatment.

Therefore, 5-FU alone cannot regulate tumour growth but, in synergy with TS/PP, it has potent immunosensitising activity in target cells due to its modulation of TS.

Furthermore, the obtained results do not indicate any autoimmunity or toxicity phenomena induced by TS/PP treatment, in the absence of secondary effects.

REFERENCES

1. Van der Wilt C L, Peters G J. Pharm World Sci 1994; 84-103
2. Chu E, Allegra C J. Bioassay 1996; 18:191-198.
3. Parsel L A, Chu E. Cancer J Sci Am 1998; 4:287-295.
4. Ju J, Pedersen. Lane J, Maley F, Chu E. Proc Natl Acad Sci 1999; 96; 3769-3774.
5. 6. Chu E, Mota A C, Fogarasi M C (2001) Antimetabolites. In: De Vita V, Hellman S, Rosenberg S A. *Cancer Principles and Practice of Oncology.* 6$^{th}$ Edition. Philadelphia: Lippincott Williams and Wilkins pg. 388-415.
7. Van der Wilt C L, Peters G J. Pharm World Sci 1994; 84-103.
8. Peters G J, Jansen G. Resistance to antimetabolites. In: Schilsky R L, Milano G A, Ratain M J, eds. *Principles of Antineoplastic Drug Development and Pharmacology.* New York: Marcel Dekker, Inc. 1996:543-585
9. Landis D M, Loeb L A. J. Biol Chem 1998; 273:31209-31214.
10. Chu E, Mota A C, Fogarasi M C (2001) Antimetabolites. In: De Vita V, Hellman S, Rosenberg S A. *Cancer Principles and Practice of Oncology.* 6$^{th}$ Edition. Philadelphia: Lippincott Williams and Wilkins pg. 388-415.
11. Storkus W J, Howell D N, Salter R D, et al. J. Immunol. 1987; 138:1657-9.
12. Correale P, Aquino A, Pellegrini M, et al. Int J Cancer in press, 2003.
13. Correale P, Sabatino M, Cusi M G, et al. J Chemother, October; 13(5):519-526, 2001
14. Parker, K. C., Bednarek, M. A. and J. E. Coligan. J Immunol 152:163-175, 1994.
15. Francini G, Scardino A, Kosmatopoulos K, et al. J. Immunol, 169:4840-4849, 2002
17. Guadagni F, Witt P L, Robbins P F, Schlom J, Greiner W J. Cancer Res. 1990; 50:6248-6255.
18. Schneck, J O, Slansky J E, O'Herrin S M et al: Monitoring antigen-specific T cells using MHC-Ig dimmers. Coligan J, Kruisbeek A M, Margulies D, Shevach E M, Strober (eds). In *Current Protocols in Immunology.* Inc. New York, N.Y. John Wiley & Sons, 200, pp 17.2.1-17.2.17.

The invention claimed is:

1. An isolated multiepitope peptide consisting of the amino acid sequence YMIAHITGLFLDSLGFSTTLGDAHIYL (SEQ ID NO: 2).

2. A pharmaceutical composition comprising a pharmaceutically effective amount of the peptide according to claim 1, and appropriate excipients and/or diluents and/or solubilising agents.

3. The pharmaceutical composition according to claim 2 further comprising an antitumor drug.

4. The pharmaceutical composition according to claim 3 wherein said anti-tumor drug is 5-fluorouracil.

* * * * *

SEQUENCE LISTING

<160> NUMBER OF SEQ ID NOS: 3

<210> SEQ ID NO 1
<211> LENGTH: 81
<212> TYPE: DNA
<213> ORGANISM: Artificial
<220> FEATURE:
<223> OTHER INFORMATION: nucleotide coding sequence of TS/PP peptide
<220> FEATURE:
<221> NAME/KEY: CDS
<222> LOCATION: (1)..(81)

```
<400> SEQUENCE: 1 tac atg att gcg cac atc acg ggc ctg ttt ttg gac agc ctg gga ttc     48
Tyr Met Ile Ala His Ile Thr Gly Leu Phe Leu Asp Ser Leu Gly Phe
1               5                   10                  15 tcc acc act ttg gga gat gca cat att tac ctg                         81
Ser Thr Thr Leu Gly Asp Ala His Ile Tyr Leu
            20                  25

<210> SEQ ID NO 2
<211> LENGTH: 27
<212> TYPE: PRT
<213> ORGANISM: Artificial
<220> FEATURE:
<223> OTHER INFORMATION: Synthetic Construct

<400> SEQUENCE: 2

Tyr Met Ile Ala His Ile Thr Gly Leu Phe Leu Asp Ser Leu Gly Phe
1               5                   10                  15

Ser Thr Thr Leu Gly Asp Ala His Ile Tyr Leu
            20                  25

<210> SEQ ID NO 3
<211> LENGTH: 9
<212> TYPE: PRT
<213> ORGANISM: Artificial
<220> FEATURE:
<223> OTHER INFORMATION: synthetic control peptide CAP-1

<400> SEQUENCE: 3

Tyr Leu Ser Gly Ala Asn Leu Asn Leu
1               5
```